(12) United States Patent
Zhang

(10) Patent No.: US 8,457,724 B2
(45) Date of Patent: Jun. 4, 2013

(54) SYSTEM FOR HEART PERFORMANCE CHARACTERIZATION AND ABNORMALITY DETECTION

(75) Inventor: Hongxuan Zhang, Palatine, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 491 days.

(21) Appl. No.: 12/610,267

(22) Filed: Oct. 30, 2009

(65) Prior Publication Data

US 2010/0152598 A1  Jun. 17, 2010

Related U.S. Application Data

(60) Provisional application No. 61/121,739, filed on Dec. 11, 2008.

(51) Int. Cl.
*A61B 5/04* (2006.01)
(52) U.S. Cl.
USPC .......................................................... 600/509
(58) Field of Classification Search
USPC ................ 600/515, 516, 517, 518; 607/4–26
See application file for complete search history.

(56) References Cited

U.S. PATENT DOCUMENTS

| | | | |
|---|---|---|---|
| 4,681,117 A | 7/1987 | Brodman et al. | |
| 4,798,211 A | 1/1989 | Goor et al. | |
| 4,924,875 A | 5/1990 | Chamoun | |
| 4,930,075 A | 5/1990 | Kortas | |
| 5,054,496 A | 10/1991 | Wen et al. | |
| 5,159,932 A | 11/1992 | Zanetti et al. | |
| 5,365,426 A | 11/1994 | Siegel et al. | |
| 6,024,705 A | 2/2000 | Schlager | |
| 6,112,116 A | 8/2000 | Fischell et al. | |
| 6,304,773 B1 * | 10/2001 | Taylor et al. | 600/515 |
| 6,339,720 B1 | 1/2002 | Anzellini et al. | |
| 6,368,284 B1 | 4/2002 | Bardy | |
| 6,424,860 B1 | 7/2002 | Karlsson et al. | |
| 6,468,263 B1 | 10/2002 | Fischell et al. | |
| 6,501,983 B1 | 12/2002 | Natarajan et al. | |

(Continued)

OTHER PUBLICATIONS

Stuart E. Sheifer, MD; Teri A. Manolio, MD,PhD; and Bernard J. Gersh, MB,ChB, DPhil "Unrecognized Myocardial Infarction", Annals of Internal Medicine, Nov. 6, 2001, vol. 135, No. 9, pp. 801-811.

(Continued)

*Primary Examiner* — Christopher D Koharski
*Assistant Examiner* — Nadia Ahmad
(74) *Attorney, Agent, or Firm* — Alexander J. Burke

(57) ABSTRACT

A system for heart performance characterization and abnormality detection, includes an acquisition device for acquiring an electrophysiological signal representing a heart beat cycle of a patient heart. A detector detects multiple parameters of the electrophysiological signal comprising at least one of, (a) amplitude, (b) time duration, (c) frequency and (d) time-frequency, representative parameters. A signal analyzer calculates at least one ratio of the detected parameters from ratios including, (i) ratio of T wave amplitude to P wave amplitude, (ii) ratio of time duration of ST wave to time duration of PR wave, (iii) ratio of a frequency of a PR wave to a frequency of a RT wave and (iv) ratio of a time-frequency measure of a PR wave to a time-frequency measure of a RT wave. A comparator determines whether a calculated ratio exceeds a predetermined upper limit threshold or a predetermined lower limit threshold. An output processor generates data representing an alert message in response to the calculated ratio exceeding a predetermined threshold.

18 Claims, 10 Drawing Sheets

U.S. PATENT DOCUMENTS

| | | | |
|---|---|---|---|
| 6,615,083 B2 * | 9/2003 | Kupper | 607/25 |
| 6,882,883 B2 | 4/2005 | Condie et al. | |
| 7,072,708 B1 | 7/2006 | Andresen et al. | |
| 7,181,268 B2 | 2/2007 | Sheldon et al. | |
| 7,225,013 B2 * | 5/2007 | Geva et al. | 600/513 |
| 7,225,015 B1 | 5/2007 | Min et al. | |
| 7,231,244 B2 | 6/2007 | Laitio et al. | |
| 7,266,410 B2 | 9/2007 | Chen | |
| 7,277,745 B2 | 10/2007 | Thakor et al. | |
| 7,299,087 B2 | 11/2007 | Bardy | |
| 7,361,473 B2 | 4/2008 | Valkirs et al. | |
| 7,415,307 B2 | 8/2008 | Sharma et al. | |
| 2004/0215090 A1 * | 10/2004 | Erkkila et al. | 600/515 |
| 2006/0004414 A1 * | 1/2006 | Chen | 607/3 |

OTHER PUBLICATIONS

S Abboud, RJ Cohen, A Selwyn, p. Ganz, D Sadeh and PL Friedman, "Detection of Transient Myocardial Ischemia by Computer analysis of Standard and Signal-Averaged High-Frequency Electrocardiograms in Patients Undergoing Percutaneous Transluminal Coronary Angioplasty", Circulation, vol. 76, pp. 585-596.

* cited by examiner

| SIGNAL PORTION | CARDIAC FUNCTION | CALCULATION ALGORITHM |
|---|---|---|
| $A_P$ | P WAVE AMPLITUDE WHICH IS STABLE AT ISCHEMIA EVENTS | $A_P$ CAN BE USED AS MAGNITUDE BASELINE ISCHEMIA DETECTION |
| $A_{base}$ | SIGNAL BASELINE DEVIATION WHICH CAN INDICATE THE CONDUCTING ENERGY LOSING | $ratio\_1 = \dfrac{A_{base}}{A_P}$ |
| $A_T$ | T WAVE AMPLITUDE WHICH CAN SHOW THE SINGLE CHANGES AT REPOLARIZATION | $ratio\_2 = \dfrac{A_T}{A_P}$ |
| $A_R$ | R WAVE AMPLITUDE WHICH CAN SHOW THE SINGLE CHANGES AT DEPOLARIZATION | $ratio\_3 = \dfrac{A_R}{A_P}$ <br> $ratio\_4 = \dfrac{A_R}{A_T}$ |
| PR | DURATION OF THE P TO R WAVE WHICH IS USUALLY STABLE DURING ISCHEMIA | QR TIME DURATION IS STABLE AND CAN BE AS DURATION BASELINE FOR ISCHEMIA DETECTION |
| RT | DURATION OF THE R TO T WAVE WHICH IS USUALLY CHANGING WITH ISCHEMIA | $ratio\_5 = \dfrac{T_{RT}}{T_{PR}}$ |
| RS | DURATION OF THE R TO S WAVE WHICH IS USUALLY CHANGING WITH ISCHEMIA | $ratio\_6 = \dfrac{T_{RS}}{T_{PR}}$ |
| ST | DURATION OF THE S TO T WAVE WHICH IS USUALLY CHANGING WITH ISCHEMIA | $ratio\_7 = \dfrac{T_{ST}}{T_{PR}}$ |
| QS | DURATION OF THE Q TO S WAVE WHICH IS USUALLY PARTIALLY CHANGING WITH ISCHEMIA | $ratio\_8 = \dfrac{T_{QS}}{T_{PR}}$ <br> $ratio\_9 = \dfrac{T_{QS}}{T_{ST}}$ |
| $f_{PR}$ | FREQUENCY ANALYSIS OF PR PORTION SIGNALS, INCLUDING DOMINANT (PRIMARY) FREQ, AVERAGING FREQ, ETC | $ratio\_10 = \dfrac{f_{PR}}{f_{RT}}$ |
| $f_{RT}$ | FREQUENCY ANALYSIS OF RT PORTION SIGNALS, INCLUDING DOMINANT (PRIMARY) FREQ, AVERAGING FREQ, ETC | THIS RATIO CAN BE DOMINANT FREQ COMPARISON OR AVERAGE FREQ COMPARISON |
| $W_{PR}$ | TIME FREQUENCY ANALYSIS FOR PR PORTION SIGNALS | $ratio\_11 = \dfrac{W_{PR}}{W_{RT}}$ |
| $W_{RT}$ | TIME FREQUENCY ANALYSIS FOR RT PORTION SIGNALS | THIS RATIO IS FOR ROI REGION COMPARISON THE TIME-FREQ DOMAIN ANALYSIS (SEE FIG. 4.) |

FIG. 6

SYSTEM FOR HEART PERFORMANCE CHARACTERIZATION AND ABNORMALITY DETECTION

This is a non-provisional application of provisional application Ser. No. 61/121,739 filed Dec. 11, 2008, by H. Zhang.

FIELD OF THE INVENTION

This invention concerns a system for heart performance characterization and abnormality detection involving calculating ratios of amplitude, time duration, frequency and time-frequency, representative parameters, for example, of an electrophysiological signal representing a heart beat cycle of a patient heart.

BACKGROUND OF THE INVENTION

Coronary Artery Disease (CAD) and heart-related problems and cardiac arrhythmias are serious illnesses. A 12-lead electrocardiogram (ECG) and multi-channel intra-cardiac electrograms (ICEG) provide diagnostic reference standards and criteria for evaluating cardiac rhythm and events. Currently waveform morphologies and time domain parameter analysis, such as P wave, QRS complex, ST segment, T wave, are used for cardiac arrhythmia monitoring and identification, such as atrial fibrillation (AF), myocardial ischemia (MI) and ventricular tachycardia/fibrillation (VT/VF), for example. However, the waveform morphologies and time domain parameter analysis are sometimes subjective and time-consuming, and require extensive expertise and clinical experience for accurate interpretation and proper cardiac rhythm management.

Some known systems apply more sophisticated mathematical theories to biomedical signal interpretation, such as frequency analysis, symbolic complexity analysis and signal entropy evaluation. But such known systems typically focus on generating a new pathology index for qualitative cardiac arrhythmia characterization, in which the data variance and statistical characteristics of the time varying signals (ECG and ICEG) have not been determined, diagnosed and evaluated. Additionally, cardiac electrophysiological (EP) activities and signals (ECG and ICEG) are time varying and known signal calculation and related analysis usually fails to localize a malfunction severity and trend of cardiac events (e.g., myocardial ischemia and infarction), such as cardiac pathology irregularity stages, arrhythmia occurrence and drug delivery response, for example.

Further, known system diagnosis and interpretation of cardiac signals based on an electrophysiological signal waveform and morphology require extensive clinical knowledge and experience. Inaccurate and subjective evaluation and diagnosis may cause unexpected delay in cardiac rhythm management, such as drug delivery and emergency treatment. Known system diagnosis and evaluation of a cardiac signal typically uses time domain parameters to diagnose and evaluate myocardial events, such as ST segment voltage deviation for ischemia detection (e.g. 0.1 mV elevation is a clinical standard for myocardial ischemia (MI) detection). However this MI analysis only works for surface ECG signals, but not for intracardiac electrograms and the ST segment deviation (voltage) cannot be utilized as a quantitative method for myocardial ischemia severity diagnosis and characterization. ST segment analysis in known clinical applications detects and evaluates MI or infarction events using a repolarization procedure signal portion within a heart beat. Information concerning a depolarization procedure is not efficiently utilized in known systems for ischemia and infarction characterization which depend on patient responses (such as chest pain, discomfort) using signal recordings and physician interpretation, however, there are many ischemia and infarction cases which are non-symptomatic. A system according to invention principles addresses these deficiencies and associated problems.

SUMMARY OF THE INVENTION

A system analyzes cardiac electrophysiological signals by determining signal ratios of both cardiac depolarization and repolarization procedures involving comparisons of both voltage and duration of depolarization and repolarization within a single heart beat cycle, for use in real time monitoring and analysis, such as in an application of implantable devices. A system for heart performance characterization and abnormality detection, includes an acquisition device for acquiring an electrophysiological signal representing a heart beat cycle of a patient heart. A detector detects multiple parameters of the electrophysiological signal comprising at least one of, (a) amplitude, (b) time duration, (c) frequency and (d) time-frequency, representative parameters. A signal analyzer calculates at least one ratio of the detected parameters from ratios including, (i) ratio of T wave amplitude to P wave amplitude, (ii) ratio of time duration of ST wave to time duration of PR wave, (iii) ratio of a frequency of a PR wave to a frequency of a RT wave and (iv) ratio of a time-frequency measure of a PR wave to a time-frequency measure of a RT wave. A comparator determines whether a calculated ratio exceeds a predetermined upper limit threshold or a predetermined lower limit threshold. An output processor generates data representing an alert message in response to the calculated ratio exceeding a predetermined threshold.

BRIEF DESCRIPTION OF THE DRAWING

FIG. 6 shows a Table indicating parameters derived within a single heart beat of an electrophysiological signal for myocardial medical condition and severity characterization, according to invention principles.

DETAILED DESCRIPTION OF THE INVENTION

Figure 1:
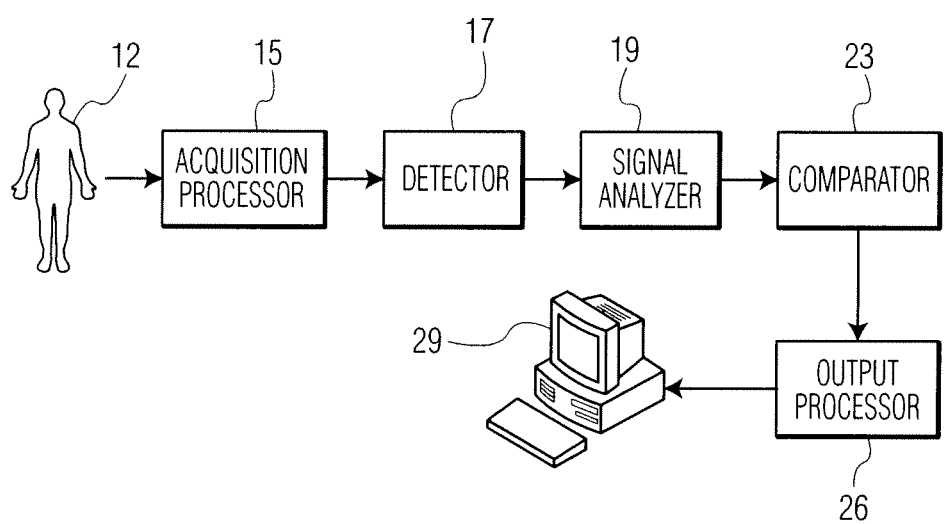
FIG. 1 shows a system for heart performance characterization and abnormality detection, according to invention principles.

Myocardial ischemia and infarction detection and analysis are valuable for the management of cardiac disorders and irregularities, which are caused by a lack of blood, or oxygen, for example, in heart tissue and cells. Usually, surface ECG signal analysis based on waveform morphology and time domain parameters is used for myocardial ischemia and infarction detection and characterization, such as ST segment or T wave changes (repolarization). However known quantitative methods for myocardial status detection and characterization, such as quantitative characterization of ongoing myocardial ischemia events and chest pain severity, are inefficient and limited in capability. A system analyzes cardiac electrophysiological signals (including surface ECG signals and internal cardiac electrograms, ICEG signals) using signal ratios associated with both cardiac depolarization and repolarization procedures to improve identification of cardiac disorders, differentiate cardiac arrhythmia irregularities, characterize pathological severity, and potentially predict life-threatening events. The signal ratio measurement and calculation include comparisons of both voltage and duration of depolarization and repolarization within a single heart beat, for use in real time monitoring and analysis, such as in the application of implantable devices.

Known MI and infarction analysis and characterization systems focus on the time domain signals (e.g. the signal magnitude voltage) and waveform morphology (such as ST segment increase or decrease) changes. Further, the information hidden in the signals is not fully used, such as frequency analysis and energy comparisons for depolarization and repolarization procedures. The inventor has recognized that MI and infarction analysis and diagnosis depends on patient responses (such as chest pain, discomfort) signal recordings and physician interpretation. However, many ischemia and infarction cases are non-symptomatic and would benefit from quantitative methods for sensitive and reliable diagnosis.

In the heart, once a cell generates an electrical impulse, this electrical impulse causes ions to cross a cell membrane and causes an action potential also called depolarization Repolarization comprises return of the ions to their previous resting state, which corresponds with relaxation of myocardial muscle. A system provides signal ratios of cardiac depolarization and repolarization procedures and captures and characterizes additional cardiac function related information, in addition to current clinical diagnosis employing waveform morphology, time domain analysis, frequency analysis and energy analysis and evaluation. The signal ratios of the cardiac depolarization and repolarization procedures more precisely detect myocardial ischemia related changes, by analyzing and diagnosing the changes of the cardiac tissue working and signal constructions, such as ischemic tissue delaying the pacing excitation transmission and broadening repolarization and partial depolarization processes. For example, RS wave and ST wave signal changes are used for detection of MI events. The signal ratios associated with cardiac depolarization and repolarization procedures advantageously provide real time analysis and detection of myocardial arrhythmias, such as ischemia and infarction, in addition to the known standard method involving determining whether an ST segment (repolarization portion) exceeds a 0.1 mV threshold for ischemia event detection of emerging myocardial ischemia events.

The system involves data representing ST segment changes and the whole heart beat electrophysiological operation, e.g., depolarization and repolarization. The signal ratio method for cardiac status monitoring, diagnosis and characterization require limited calculation and computation resources, desirable for an implantable device and portable system in cardiac applications, such as ICDs (Intra-cardiac devices) and Holster monitoring. Myocardial ischemia or infarction reduces blood flow to regions of the heart, where cells respond by altering the action potential. The changes in these individual cells manifest in the local electrograms during depolarization and repolarization, reducing signal energy (hyperkalemia or anoxia) or creating multi-phasic waveforms (decoupling). These abnormal behaviors in relatively small regions of the heart, lumped together with the rest of the heart, cause notches and slurs of small amplitude superimposed on a largely normal electrograms, both surface ECG signals and intra-cardiac electrograms.

FIG. 1 shows system 10 for heart performance characterization and abnormality detection. System 10 uses signal ratios of the same cardiac heart beat signal to diagnose the electrophysiological activities of the heart tissue and function status. Most action potentials within the heart are happening in two procedures, depolarization and repolarization, within the 4 chambers. The action potentials from the heart cells and tissues accumulate and are employed in constructing the heart electrograms, which are known as ECG (from surface) and intra-cardiac electrograms. Hence different portions of the electrograms indicate cardiac activities of corresponding areas and tissue. For example, a P wave represents action potential and activities of atrial tissue and muscles while a QRS complex represents transition of the cardiac excitation from atrium to ventricle. Furthermore, the action potentials, even in the same section (e.g. the QRS complex), may represent different kinds of procedure, such as QR portion and RS portion. For ischemia and infarction monitoring and event characterization, the precise portion of the electrophysiological signals are accurately extracted and analyzed by system 10.

Acquisition device (processor) 15 acquires an electrophysiological signal representing a heart beat cycle of a heart of patient 12. Detector 17 detects multiple parameters of the electrophysiological signal comprising, amplitude, time duration, frequency and time-frequency, representative parameters. Signal analyzer 19 calculates at least one ratio of the detected parameters from ratios including, (i) ratio of T wave amplitude to P wave amplitude, (ii) ratio of time duration of ST wave to time duration of PR wave, (iii) ratio of a frequency of a PR wave to a frequency of a RT wave and (iv) ratio of a time-frequency measure of a PR wave to a time-frequency measure of a RT wave. Comparator 23 determines whether a calculated ratio exceeds a predetermined upper limit threshold or a predetermined lower limit threshold. Output processor 26 generates data representing an alert message in response to the calculated ratio exceeding a predetermined threshold for display on workstation 29, for example. In one embodiment, the system according to invention principles provides a "YES or NO" indication of occurrence of an ischemia procedure and also provides an indication of severity and prediction of possible myocardial ischemia events.

Figure 2:
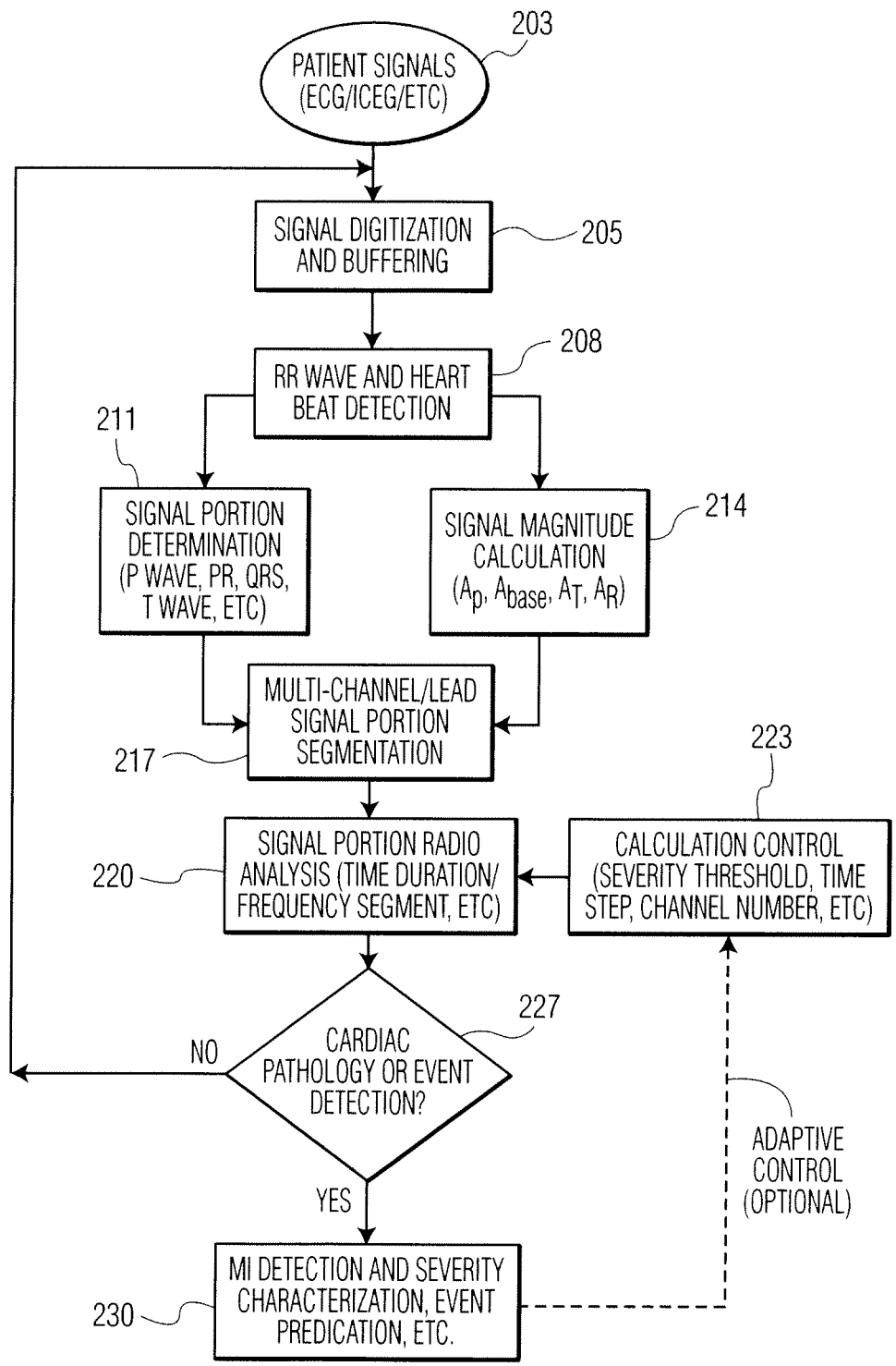
FIG. 2 shows a flowchart of a process used by a system for heart performance characterization and abnormality detection, according to invention principles

FIG. 2 shows a flowchart of a process used by system 10 for heart performance characterization and abnormality (e.g., myocardial ischemia and infarction) detection using real time signal ratio calculation and analysis. System 10 determines signal ratios for myocardial ischemia and infarction detection and characterization using different kinds of signal portion ratio including time domain (such as P wave, R wave) and frequency domain ratios. Different methods are employed for signal portion ratio calculation and computation. In step 203 acquisition processor 15 (FIG. 1) acquires signals from patient 12 such as ECG and ICEG signals and buffers, digitizes and filters the signals in step 205. In step 208 detector 17 pre-analyzes the digitized, filtered signals to detect a QRS complex (detect an RR wave and heart cycle). Detector 17 in step 211 identifies and detects different portions of a heart cycle including P wave, PR, QRS, T wave segments and associated parameters. In step 214 detector 17 determines parameters comprising signal amplitude of a P wave, signal baseline, T wave and R wave ($A_P, A_{base}, A_T, A_R$), for example. Detector 17 in step 217 performs identification and detection of different parameters of different portions of a heart cycle for individual channels of a multi-lead intra-cardiac (e.g., basket type) catheter and associated parameters, for example.

Signal analyzer 19 in step 220 calculates ratios of the detected parameters shown in the Table of FIG. 6. Specifically, analyzer 19 calculates time domain signal portion ratios of the determined parameters including PR, RT, $A_P$, $A_T$ (items 607, 609, 603 and 605 respectively of FIG. 6) ratios, for example. Analyzer 19 also calculates frequency domain and time-frequency joint domain cardiac signal analysis ratios including $f_{PR}, f_{RT}, W_{PR}, W_{RT}$ (items 613, 615, 617 and 619 respectively of FIG. 6). Analyzer 19 performs real time analysis and diagnosis to detect and characterize ischemia. Comparator 23 in step 227 determines whether a calculated ratio exceeds a predetermined upper limit threshold or a predetermined lower limit threshold to identify a particular cardiac condition or event. In response to absence of detection of a particular cardiac condition or event in step 227, unit 23 initiates iterative repetition of the FIG. 2 process from step 205. In response to detection of a particular cardiac condition or event in step 227, unit 23 in step 230 records detection of MI (Myocardial Infarction), severity and cardiac events and predicts cardiac events, for example and in step 223 adaptively adjusts system 10 operation by adjusting detection thresholds, severity thresholds, time step increment used in calculation, and multi-channel catheter channel number. Signal analyzer 19 calculates ratios of the detected parameters using a control parameter, such as a severity threshold or calculation time step, for example, provided by user input or by an executable application adaptively adjusting calculation. Output processor 26 generates data representing an alert message for display on workstation 29 in response to the calculated ratios exceeding a predetermined threshold.

System 10 performs time domain, frequency and time-frequency domain joint signal ratio analysis for cardiac ischemia analysis, diagnosis and characterization independently of, and in addition to, known calculations. For example, time domain analysis, such as signal amplitude and duration ratios, are usable in implantable cardiac device, which require low complexity algorithms and simple calculations methods. The system performs signal ratio base ischemia detection and analysis to identify cardiac disorders, differentiate cardiac arrhythmias, characterize pathological severity and predict life-threatening events. Thereby, the system alters heart medical treatment, such as drug delivery and long term cardiac care (e.g. bedside cardiac monitoring system or portable patient cardiac function monitoring and analysis system, such as Holster Monitoring).

Figure 3A:
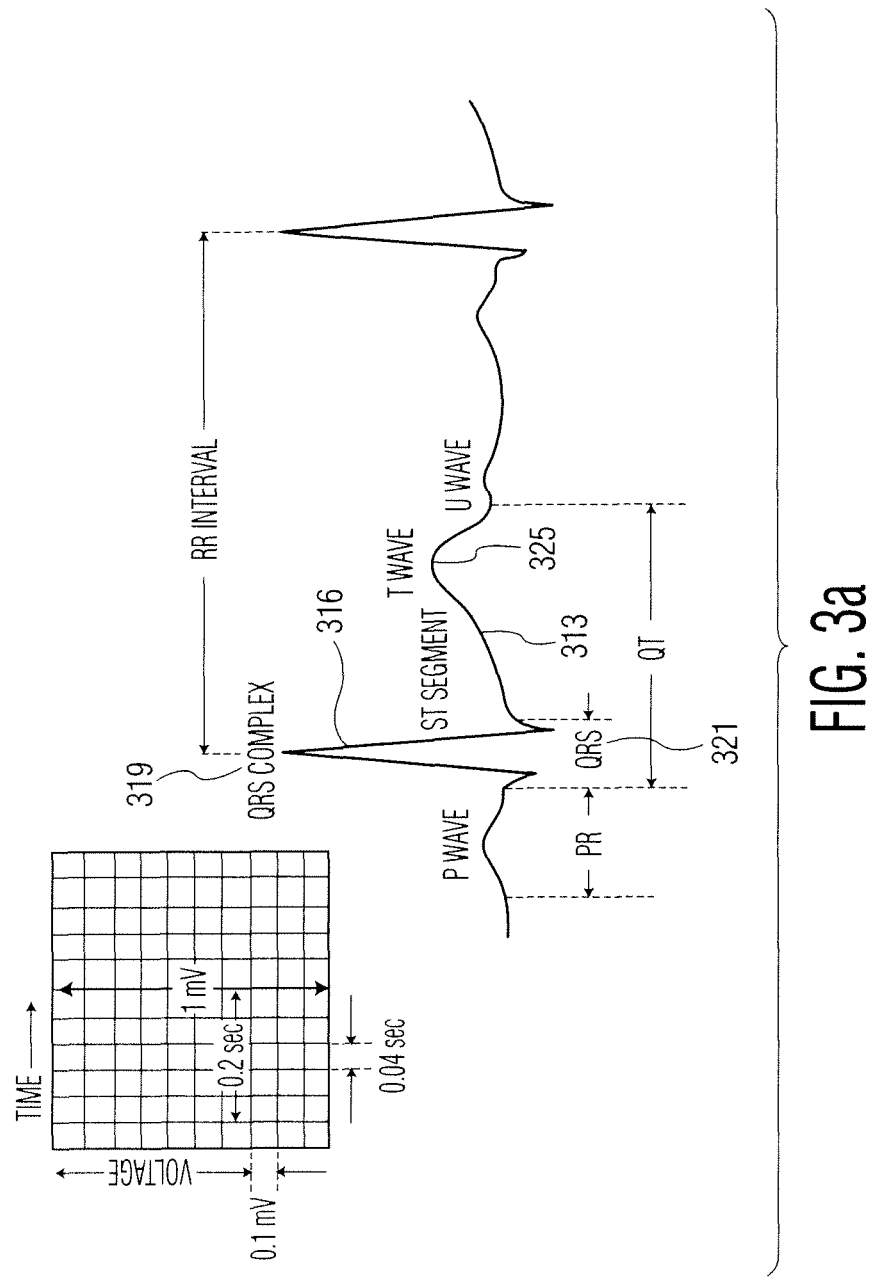
FIG. 3 illustrates electrophysiological signal changes for use in detecting medical conditions, according to invention principles.
Figure 3B:
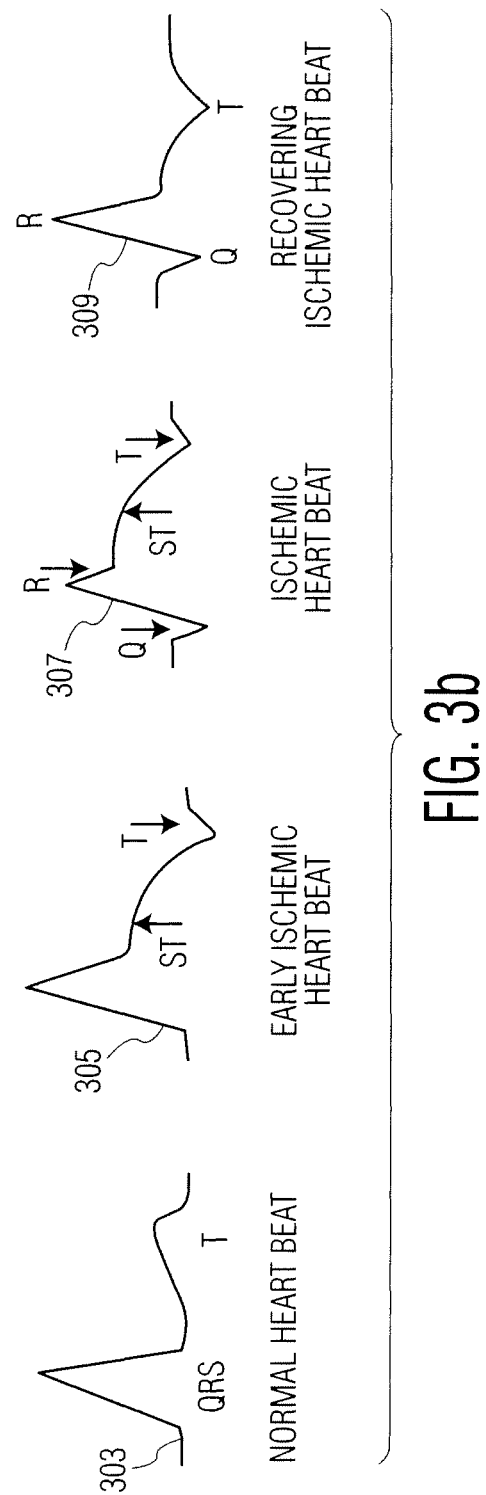

FIG. 3 illustrates electrophysiological signal changes for use in detecting medical conditions such as an ischemia event and a conducting procedure and pathway in the heart associated with depolarization and repolarization. Specifically, FIG. 3a shows action potential signals and activities, including voltage and time range, e.g. 0.1 mV indicating the threshold for ischemia events. FIG. 3b shows a progression of ischemia (lack of blood) events, from normal heart beat 303, early ischemic heart beat 305, ischemic heart beat 307 and recovering ischemic heart beat (reperfusion) 309. Electrophysiological signals indicate different types of signal deviation and changes which may be used to detect and diagnose ischemia and infarction (especially for non-symptomatic myocardial ischemia cases), including ST segment 313 change, RS portion 316 change, R wave amplitude 319 change, QS portion interval 321 change and T wave position 325 change. The system also determines frequency change within the different signal portions (including depolarization and repolarization portions). System 10 advantageously determines and uses changes in the signal portions for ischemia detection and analysis which is of particular value in cases that known ST segment analysis fails to identify.

Figure 4A:
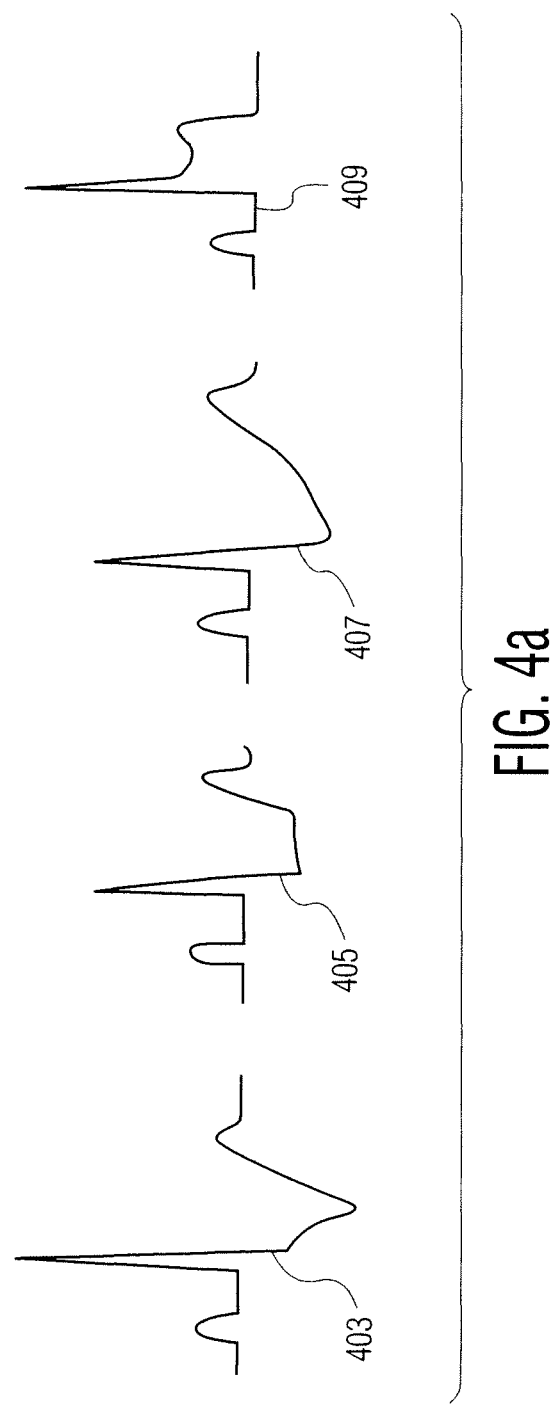
FIG. 4 illustrates different kinds of myocardial ischemia cases and corresponding electrophysiological signals.
Figure 4B:
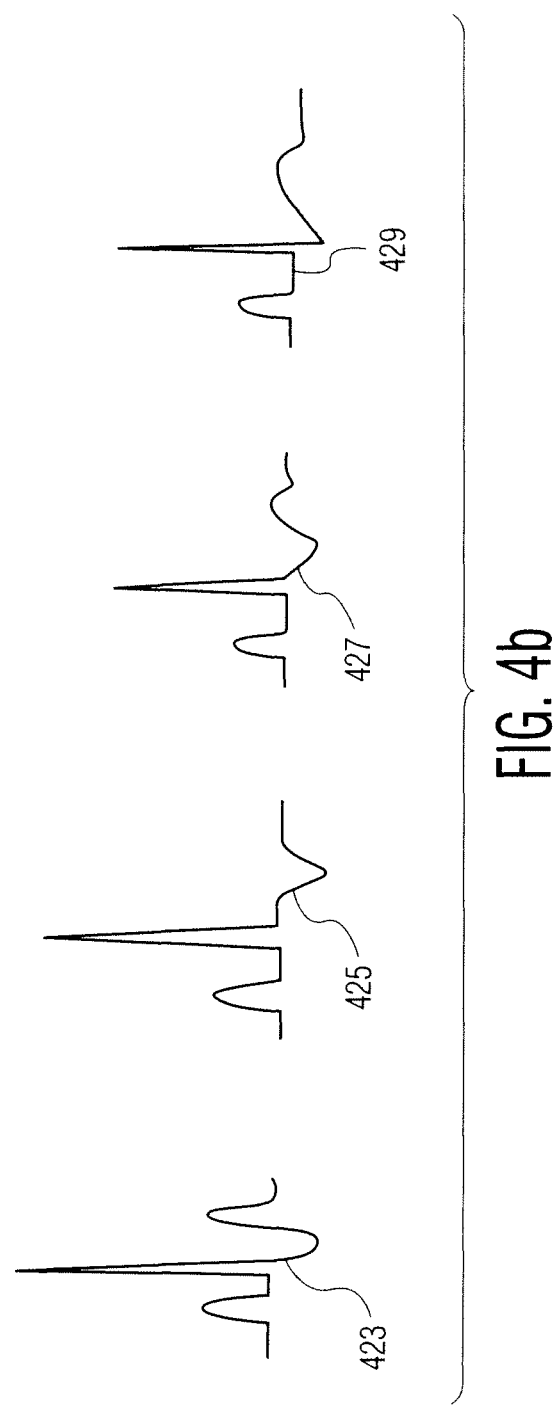

FIG. 4 illustrates different kinds of myocardial ischemia cases and corresponding electrophysiological signals. Specifically, FIG. 4a shows electrophysiological signals 403, 405, 407 and 409 exhibiting detectable ischemia events. System 10 detects ischemia in electrophysiological signals 423, 425, 427 and 429 of FIG. 4b exhibiting ischemia events undetectable using known ST segment threshold detection. The system takes advantage of numerous changes in QRS and T wave, for example, for myocardial ischemia and infarction detection and characterization.

Figure 5:
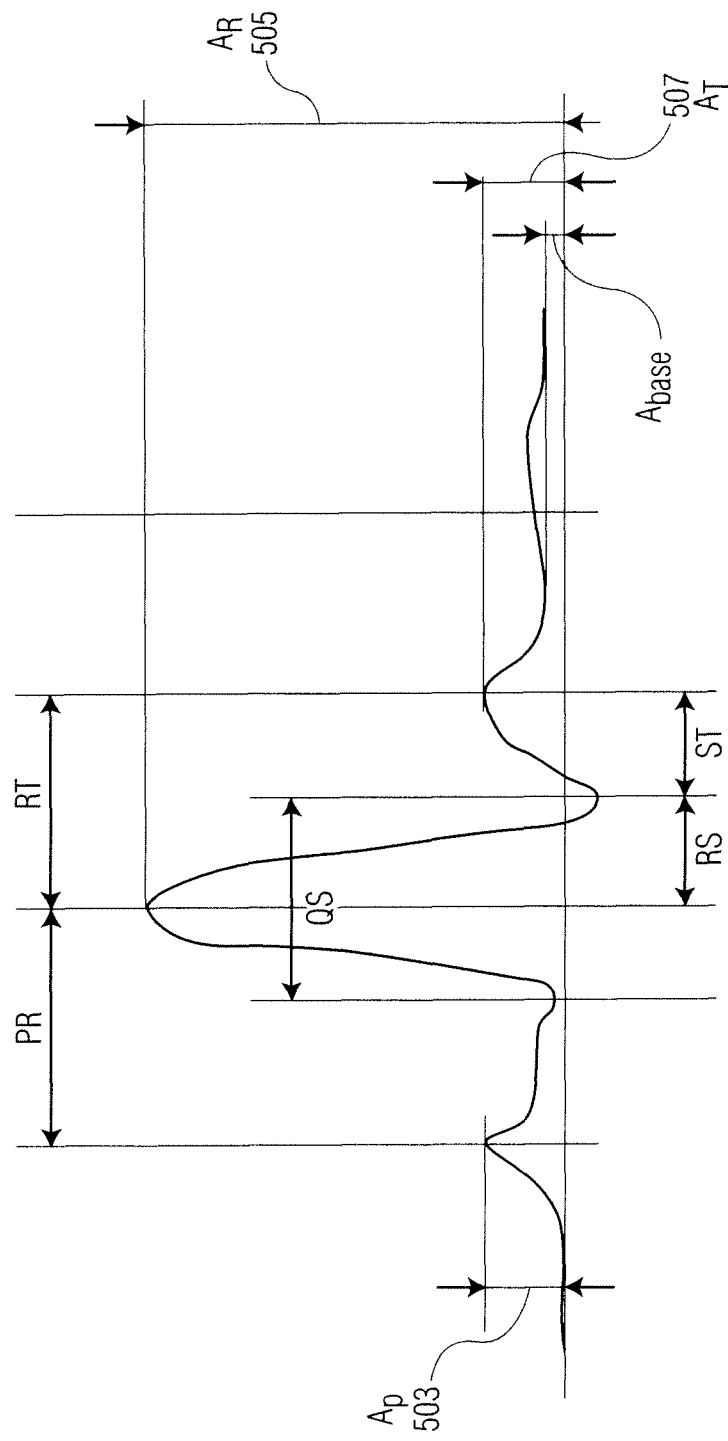
FIG. 5 illustrates different portions of a cardiac signal which may be used for ischemia detection, information extraction and condition characterization, according to invention principles.

FIG. 5 illustrates different portions of a cardiac signal which may be used for ischemia detection, information extraction and condition characterization. The different signal portions (and parameters thereof), are used individually and in combination by system 10 for ischemia detection or myocardial ischemia information extraction and characterization. For example, a P wave amplitude ($A_P$) 503 is usually stable during an ischemia or infarction event such as LAD (Left Anterior Descending Artery) occlusion and may be used to find the ischemia by being compared with $A_R$ 505 or $A_T$ 507 amplitudes. System 10 calculates the parameters identified in the Table of FIG. 6, to detect, analyze, characterize and predict myocardial ischemia and infarction events. The time duration parameters of the Table of FIG. 6 are from signal Peak to signal Peak, e.g., PR duration 607 is the time from the peak time of a P wave to peak time of an R wave.

The FIG. 6 parameters are used by system 10 in ischemia detection based on cardiac procedure comparison between depolarization and repolarization. System 10 detects ischemic events in ventricular regions, in which the electrophysiological signals of the atrium are not substantially affected. System 10 is not limited to any particular ischemia or infarction but may be used for any kind of cardiac arrhythmia detection, analysis, diagnosis and characterization. System 10 uses the parameters of FIG. 6, for qualitative detection and determination of myocardial ischemia and infarction as well as for quantitative diagnosis and characterization of myocardial ischemia and infarction, such as severity and time parameters. The system also predicts ischemia or infarction events providing values supporting early diagnosis and medical treatment.

Figure 7:
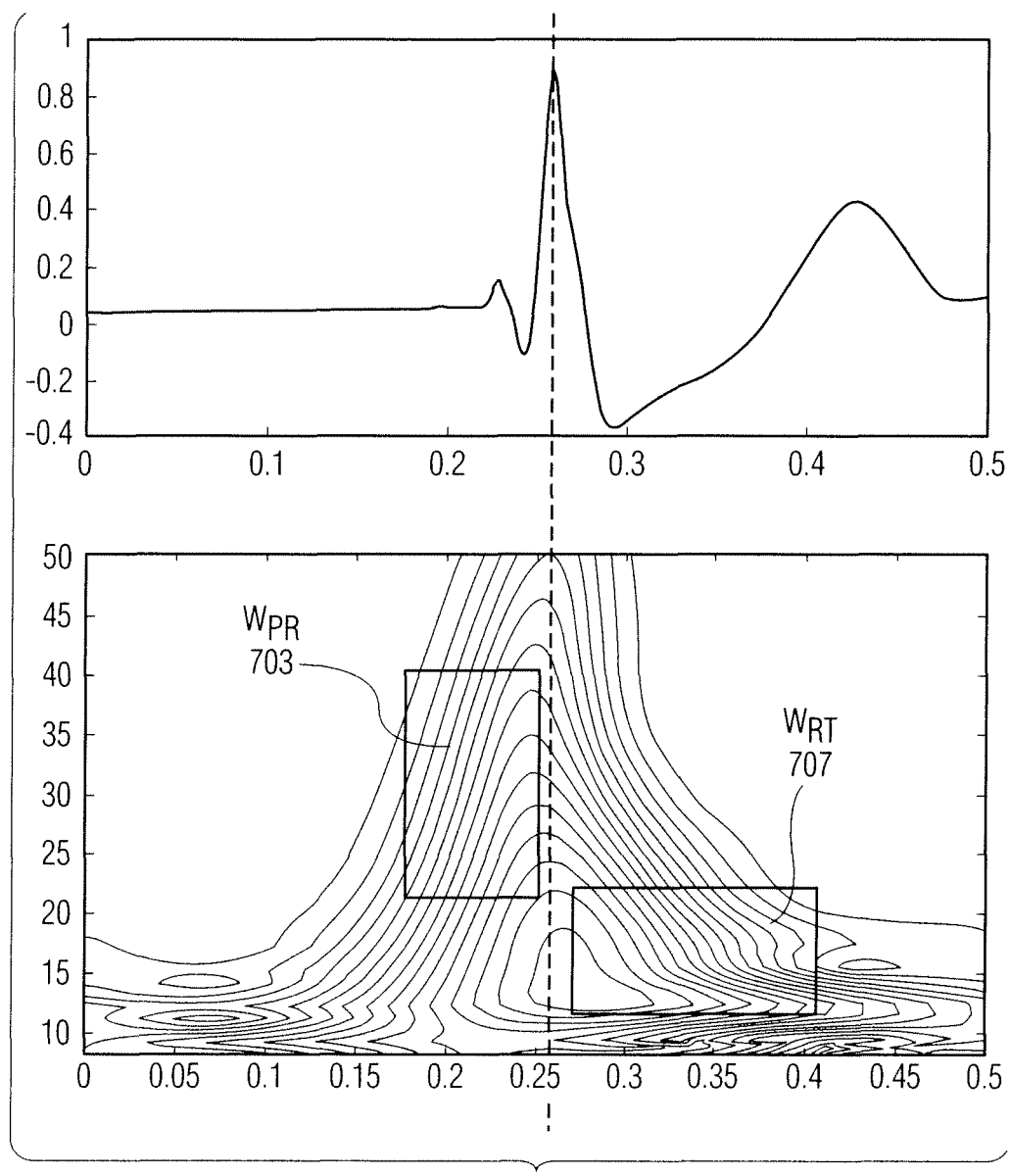
FIG. 7 illustrates a time frequency joint domain analysis and distribution for a cardiac signal, according to invention principles.

FIG. 7 illustrates a time frequency joint domain analysis and distribution for a cardiac signal. In the time frequency distribution, $W_{PR}$ 703 represents a stable portion of signals during ischemia events and $W_{RT}$ 707 (including ST portion signals) is used for illustration of sensitive and accurate quantification of ischemia. System 10 adaptively adjusts window size (both in time duration and frequency bandwidth) in response to application type and environment (such as a noise level). For example, system 10 analyzes a QRS segment portion using a 25-40 Hz window. The ratio of the time frequency window of a ROI (region of interest) for myocardial ischemia and infarction does not rely on a pre-determined baseline (or benign signals) and may be used independently and in real time. Typically the calculation window size for $W_{PR}$ is a frequency bandwidth of 20-45 Hz and QR time duration portion 50-100 ms. The calculation window size for $W_{RT}$ is a frequency bandwidth of 5-25 Hz, and QR time duration portion 50-200 ms, for example. $W_{PR}$ and $W_{RT}$ comprise electrical potentials determined by filtering a cardiac signal using a bandpass filter, in one embodiment. In other embodiments different digital or analog filters may be used such as low pass and high pass.

Figure 8:
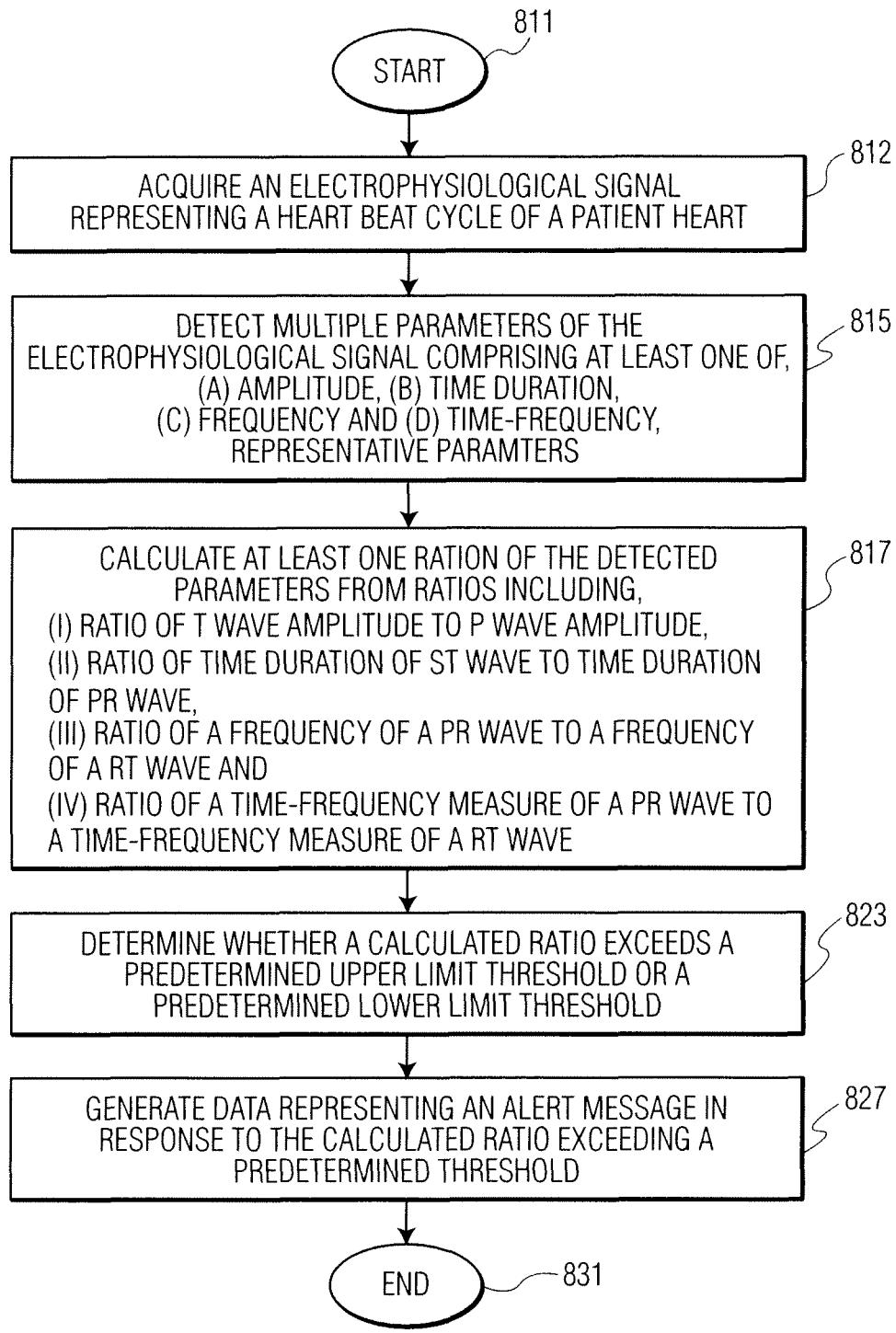
FIG. 8 shows a flowchart of a process used by a system for heart performance characterization and abnormality detection, according to invention principles.

FIG. 8 shows a flowchart of a process used by system 10, such as a patient monitoring device, for heart performance characterization and abnormality detection. In step 812 following the start at step 811, acquisition processor 15 acquires an electrophysiological signal representing a heart beat cycle of a patient heart. Detector 17 in step 815 detects multiple parameters of the electrophysiological signal comprising at least one of, (a) amplitude, (b) time duration, (c) frequency and (d) time-frequency, representative parameters. In step 817, signal analyzer 19 calculates ratios of the detected parameters indicated in FIG. 6 including one or more of, (i) ratio of T wave amplitude to P wave amplitude, (ii) ratio of time duration of ST wave to time duration of PR wave, (iii) ratio of a frequency of a PR wave to a frequency of a RT wave and (iv) ratio of a time-frequency measure of a PR wave to a time-frequency measure of a RT wave. The frequency of the PR wave and the frequency of the RT wave comprise an average frequency or a dominant frequency. The time-frequency measure of the PR wave and the time-frequency measure of the RT wave comprise electrical voltage potentials determined by detector 17 using a bandpass filter.

In step 823, comparator 23 determines whether a calculated ratio exceeds a predetermined upper limit threshold or a predetermined lower limit threshold. Output processor 26 in step 827 generates data representing an alert message in response to the calculated ratio exceeding a predetermined threshold or in response to a predetermined combination of calculated ratios exceeding a predetermined threshold. The alert message at least one of, indicates severity of a cardiac condition, provides advance warning of myocardial ischemia or acute myocardial infarction in cases including non-symptomatic cases and supports substantially real time diagnosis or treatment of a patient. The alert message also initiates treatment by at least one of, (a) initiating drug delivery and (b) initiating electrical stimulus or pacing of a heart. In one embodiment, output processor 26 is a signal generator generating a signal adjusting operation of a heart assist device comprising a heart pacing device, a defibrillator or a cardioverter. The process of FIG. 8 terminates at step 831.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A display processor or generator is a known element comprising electronic circuitry or software or a combination of both for generating display images or portions thereof.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. The system and processes of FIGS. 1-8 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system calculates parameter ratios of cardiac electrophysiological signals including both voltage and duration ratios of depolarization and repolarization functions in a single heart beat, for use in real time monitoring and analysis to improve identification of cardiac disorders, differentiate cardiac arrhythmia irregularities and characterize pathological severity. Further, the processes and applications may, in alternative embodiments, be located on one or more (e.g., distributed) processing devices on a network connecting the elements of FIG. 1. Any of the functions and steps provided in FIGS. 1-8 may be implemented in hardware, software or a combination of both.

What is claimed is:

1. A system configured for heart performance characterization and abnormality detection, comprising:
    an acquisition device configured for acquiring an electrophysiological signal representing a heart beat cycle of a patient heart;
    a detector configured for detecting a plurality of parameters of said electrophysiological signal comprising at least one of, (a) amplitude, (b) time duration, (c) frequency and (d) time-frequency, representative parameters;
    a signal analyzer configured for calculating at least one ratio of the detected parameters from ratios including,
        (i) ratio of T wave amplitude to P wave amplitude, (ii) ratio of time duration of ST wave to time duration of PR wave,
(iii) ratio of a frequency of a PR wave to a frequency of a RT wave and
(iv) ratio of a time-frequency measure of a PR wave to a time-frequency measure of a RT wave;
a comparator configured for determining whether the at least one calculated ratio exceeds a predetermined upper limit threshold or a predetermined lower limit threshold; and
an output processor configured for generating data representing an alert message in response to said calculated ratio exceeding a predetermined threshold.

2. A system according to claim 1, wherein said signal analyzer selects said frequency of said PR wave and said frequency of said RT wave to comprise at least one of, (a) an average frequency and (b) a dominant frequency.

3. A system according to claim 1, wherein said signal analyzer selects said time-frequency measure of said PR wave and said time-frequency measure of said RT wave to comprise electrical voltage potentials determined by said detector using a bandpass filter.

4. A system according to claim 1, wherein said signal analyzer selects,
said ratio of T wave amplitude to P wave amplitude to comprise $$\text{ratio\_2} = \frac{A_T}{A_P},$$

said ratio of time duration of ST wave to time duration of PR wave to comprise $$\text{ratio\_7} = \frac{T_{ST}}{T_{PR}},$$

said ratio of a frequency of a PR wave to a frequency of a RT wave to comprise $$\text{ratio\_10} = \frac{f_{PR}}{f_{RT}}$$

and
said ratio of a time-frequency measure of a PR wave to a time-frequency measure of a RT wave to comprise $$\text{ratio\_11} = \frac{W_{PR}}{W_{RT}}.$$

5. A system according to claim 1, wherein said signal analyzer additionally calculates a ratio of the detected parameters comprising $$\text{ratio\_1} = \frac{A_{base}}{A_P}.$$

6. A system according to claim 1, wherein said signal analyzer additionally calculates a ratio of the detected parameters comprising $$\text{ratio\_5} = \frac{T_{RT}}{T_{PR}}.$$

7. A system according to claim 1, wherein said signal analyzer additionally calculates a ratio of the detected parameters comprising at least one of, $$\text{(a) ratio\_3} = \frac{A_R}{A_P}$$

and $$\text{(b) ratio\_4} = \frac{A_R}{A_T}.$$

8. A system according to claim 1, wherein said signal analyzer additionally calculates a ratio of the detected parameters comprising $$\text{ratio\_6} = \frac{T_{RS}}{T_{PR}}.$$

9. A system according to claim 1, wherein said signal analyzer additionally calculates a ratio of the detected parameters comprising at least one of, $$\text{(a) ratio\_8} = \frac{T_{QS}}{T_{PR}}$$

and $$\text{(b) ratio\_9} = \frac{T_{QS}}{T_{ST}}.$$

10. A system according to claim 1, wherein said output processor generates data representing an alert message in response to a predetermined combination of calculated ratios exceeding a predetermined threshold.

11. A system according to claim 1, wherein said system comprises a patient monitoring device.

12. A system according to claim 1, wherein said output processor generates data representing said alert message indicating severity of a cardiac condition.

13. A system according to claim 1, wherein said output processor generates data representing said alert message providing advance warning of myocardial ischemia or acute myocardial infarction in cases including non-symptomatic cases.

14. A system according to claim 1, including at least one of, (a) a device for initiating drug delivery and (b) a device for initiating electrical stimulus or pacing of a heart wherein said output processor generates data representing said alert message for initiating treatment by at least one of, (a) initiating drug delivery and (b) initiating electrical stimulus or pacing of a heart.

15. A system according to claim 1, wherein said output processor generates data representing said alert message supporting substantially real time diagnosis or treatment of a patient.

16. A system configured for heart performance characterization and abnormality detection, comprising:
an acquisition device configured for acquiring an electrophysiological signal representing a heart beat cycle of a patient heart;

a detector configured for detecting a plurality of parameters of said electrophysiological signal comprising at least one of, (a) amplitude, (b) time duration, (c) frequency and (d) time-frequency, representative parameters;

a signal analyzer configured for calculating at least one ratio of the detected parameters from ratios including, (i) ratio of T wave amplitude to P wave amplitude, (ii) ratio of time duration of ST wave to time duration of PR wave, (iii) ratio of a frequency of a PR wave to a frequency of a RT wave and (iv) ratio of a time-frequency measure of a PR wave to a time-frequency measure of a RT wave;

a comparator configured for determining whether the at least one calculated ratio exceeds a predetermined upper limit threshold or a predetermined lower limit threshold; and a signal generator configured for generating a signal for adjusting operation of a heart assist device.

17. A system according to claim 16, wherein said heart assist device comprises at least one of, (a) a heart pacing device, (b) a defibrillator and (c) a cardioverter.

18. A method for heart performance characterization and abnormality detection, comprising the activities of:

acquiring an electrophysiological signal representing a heart beat cycle of a patient heart;

detecting a plurality of parameters of said electrophysiological signal comprising at least one of, (a) amplitude, (b) time duration, (c) frequency and (d) time-frequency, representative parameters;

calculating at least one ratio of the detected parameters from ratios including, (i) ratio of T wave amplitude to P wave amplitude, (ii) ratio of time duration of ST wave to time duration of PR wave, (iii) ratio of a frequency of a PR wave to a frequency of a RT wave and (iv) ratio of a time-frequency measure of a PR wave to a time-frequency measure of a RT wave;

determining whether a calculated ratio exceeds a predetermined upper limit threshold or a predetermined lower limit threshold; and generating data representing an alert message in response to said calculated ratio exceeding a predetermined threshold.

\* \* \* \* \*